(12) United States Patent
van Krieken

(10) Patent No.: US 7,002,039 B2
(45) Date of Patent: Feb. 21, 2006

(54) METHOD FOR THE PURIFICATION OF AN ALPHA-HYDROXY ACID ON AN INDUSTRIAL SCALE

(75) Inventor: Jan van Krieken, Gorinchem (NL)

(73) Assignee: Purac Biochem B.V., Gorinchem (NL)

( * ) Notice: Subject to any disclaimer, the term of this patent is extended or adjusted under 35 U.S.C. 154(b) by 0 days.

(21) Appl. No.: 10/380,535

(22) PCT Filed: Sep. 14, 2001

(86) PCT No.: PCT/NL01/00684

§ 371 (c)(1),
(2), (4) Date: Jan. 14, 2004

(87) PCT Pub. No.: WO02/22546

PCT Pub. Date: Mar. 21, 2002

(65) Prior Publication Data

US 2004/0116740 A1 Jun. 17, 2004

(30) Foreign Application Priority Data

Sep. 15, 2000 (NL) .............................. 1016204

(51) Int. Cl.
*C07C 51/42* (2006.01)

(52) U.S. Cl. ...................................... 562/580

(58) Field of Classification Search ................ 562/580
See application file for complete search history.

(56) References Cited

U.S. PATENT DOCUMENTS

| | | | |
|---|---|---|---|
| 5,510,526 A | 4/1996 | Baniel et al. | |
| 2002/0102672 A1 * | 8/2002 | Mizrahi et al. | ............. 435/139 |

FOREIGN PATENT DOCUMENTS

| | | |
|---|---|---|
| DE | 593657 | 2/1934 |
| EP | 0646399 A1 * | 9/1993 |
| EP | 0733 616 A1 | 9/1996 |
| WO | WO 92/05138 | 4/1992 |

OTHER PUBLICATIONS

W.G. Kerckhoff, "The preparation of Crystalline Lactic Acid", Jun. 7, 1933, pp. 449–460.

* cited by examiner

*Primary Examiner*—Paul A. Zucker
(74) *Attorney, Agent, or Firm*—Gilberto M. Villacorta

(57) ABSTRACT

The invention relates to a method for the purification of a fermentatively prepared α-hydroxy acid on an industrial scale, in which an α-hydroxy acid with a color (fresh) of not more than 10,000 APHA units is subjected to at least two crystallization steps, with the crystallization steps being carried out in cooling crystallization devices, melting crystallization devices, evaporative crystallization devices and/or adiabatic crystallization devices.

12 Claims, No Drawings

METHOD FOR THE PURIFICATION OF AN ALPHA-HYDROXY ACID ON AN INDUSTRIAL SCALE

The present invention relates to a method for the purification of α-hydroxy acids, in particular lactic acid or glycolic acid, on an industrial scale, as well as to products of the utmost chiral purity which can be obtained by this method, and to applications thereof.

Lactic acid is usually marketed as a dilute or concentrated solution, because lactic acid has a strong tendency to form intermolecular esters (dimeric and polymeric lactic acid). In addition, lactic acid (even very pure lactic acid) is strongly hygroscopic. The purification of lactic acid (the racemic mixture and in particular the enantiomers of lactic acid) on an industrial scale is a complicated and difficult process according to the prior art.

It is known how to produce lactic acid, or 2-hydroxypropionic acid, in a fermentative manner. In general the fermentative production of lactic acid includes first of all a fermentation step in which a carbohydrate-containing substrate such as glucose or sucrose is converted to lactic acid by a suitable microorganism. Known microorganisms producing S-lactic acid are various bacteria of the genus *Lactobacillus*, such as *Lactobacillus casei* for example. In addition microorganisms are also known which produce (R)-lactic acid selectively. The aqueous fermentation product is then processed in order to obtain lactic acid. The usual industrial processing path generally consists of separation of the biomass followed by acidification, purification and concentration.

In the case of (S)-lactic acid the lactic acid so obtained is sufficiently pure to be processed in foods for human consumption. (S)- or (R)-lactic acid which is ultimately obtained by this usual method can be 98% enantiomerically pure or even higher (i.e. 98% or more of the lactic acid present consists of the (S)- or (R)-enantiomer). The product still contains residual sugars, however. The product is also yellow in colour and on heating this becomes brown to black through decomposition of impurities. Moreover, in the case of (S)-lactic acid, the organoleptic properties often leave something to be desired. The lactic acid enantiomer is thus moderately suitable for application in foods, but on the whole not suitable for pharmaceutical applications and for synthesis of compounds.

The purity of the product can be increased by esterification followed by hydrolysis, so that it is suitable for pharmaceutical applications. As a result of this esterification/hydrolysis, however, the enantionmeric purity decreases and the lactic acid still contains a small amount of the alcohol which has been used in the esterification. Examples of other methods for the purification of lactic acid include subjecting aqueous solutions of lactic acid to one or more extraction, (steam) distillation and/or evaporation steps, electodialysis steps and crystallizaions (see for example Ullmans Encyklopädie der Technischen Chemie, Verlag Chemie GmbH, Weinheim, fourth edition, Part 17, pages 1–7 (1979); H. Benninga, "History of Lactic Acid Making", Kluwer Academic Publishers, Dordrecht-Boston-London (1990); C. H. Holten, "Lactic Acid; Properties and Chemistry of Lactic Acid and Derivatives", Verlag Chemie GmbH, Weinheim (1971); The Merck Index, Merck & Co., Inc., eleventh edition, page 842 (1989); Römmp Chemie Lexicon, G. Thieme Verlag, Stuttgart and N.Y., ninth edition, Part 4, pages 2792–2893 (1991) and the Netherlands patent applications 1013265 and 1013682.

In German Patent 593,657 (granted on 15 Feb. 1934) a laboratory experiment is described in which an aqueous solution of lactic acid, which contained an excess of the S component and practially no lactic acid anhydride, was concentrated by means of a thin-film evaporation technique, if necessary at reduced pressure. The concentrated lactic acid solution was then rapidly cooled, with formation of crystals. After that the crystals were separated from the mother liquor, washed with ether and repeatedly recrystallized from ethyl acetate or chloroform or a comparable solvent until the crystals showed a sharp melting point of 53° C. The chiral purity of the enantiomeric excess and the colour are not reported.

In H. Borsook, H. M. Huffman, Y-P. Liu, J. Biol. Chem. 102, 449–460 (1933) a laboratory experiment is described in which an aqueous mixture, which contained 50 percent lactic acid with an excess of (S)-lactic acid, 30 percent lactic acid anhydride and lactic acid dimer and 15 percent water, was subjected to fractional distillation at approximately 0.13 mbar and 105° C. The middle fraction was the distilled again and after that cooled in an ice/salt bath with formation of a solid crystal mass. It is reported that the distilliation has to be preformed with small quantities, because with larger quantities there is a big loss of product as a result of the long heating time. The solid crystal mass was then recrystallized three times from an equal volume of equal quantities of diethyl ether and diisopropyl ether, and the crystals were isolated and dried at room temperature in a vaccum drier. In this way it was possible to obtain (S)-lactic acid with a melting point of 52.7–52.8° C. which contained less than 0.1 percent impurities such as water, lactic acid anhydride or lactic acid dimer. The chiral purity or the enantomeric excess and the colour of (S)-lactic acid are not reported.

In L. B. Lockwood, D. E. Yoder, M. Zienty, Ann N.Y. Acad. Sci. 119, 854 (1965) the distillation and crystallization of lactic acid on a laboratory scale is also descibed, the melting point of the optically pure lactic acid obtained being 54° C. The colour is not reported.

In 1934 the crystallization of lactic acid was investigated by Boehringer Ingelheim, but this method was not found to give good results, owing to problems with the purification and further treatment. After the Second World War, however, it turned out that Boehringer Ingelheim was able to produce lactic acid for pharmaceutical applications on a scale of about 12 to 15 tons per month, with a yield of about 77 to 86 percent. In this process an aqueous solution of lactic acid was purified by means of steam distillation at reduced pressure (abount 13 mbar), followed by crystallization at –25° C., after which the crystals were dissolved in water and the solution was treated with potassium ferrocyanide (to remove heavy metals) and activated charcoal. The chiral purity or the enantiomeric excess or other properties such as colour and odour of the (S)-lactic acid so produced are not known (see H. Benninga, "History of Lactic Acid Making", Kluwer Academic Publishers, Dordrecht-Boston-London, pages 347–350 (1990)).

Crystalline (S)-lactic acid has been marketed by, for example, Fluka and Sigma with purities of more than 99% (see for example M. L. Buszko, E. R. Andrew, Mol. Phys. 76, 83–87 (1992) and T. S. Ing, A. W. Yu, V. Nagaraja, N. A. Amin, S. Ayache, V. C. Gandhi, J. T. Daugirdas, Int. J. Artif. Organs 17, 70–73 (1994)). Crystallic S-lactic acid with a water content of less than 1 percent by weight is known from EP A 563,455 (see Example 1). The crystal structure of lactic acid is described in A. Schouten, J. A. Kanters, J. van Krieksn, J. Mol. Stuct. 323, 165–168 (1994). Lactic acid can also be obtained in a synthetic manner. This is known. The product of the synthetic production method, however, is a racemic mixture which thus contains (S)-lactic acid and (R)-lactic acid in equal quantities. It is true that the separate enantiomers can be separated by means of known techniques, such as diastereoisomer separation techniques, where one of the enantiomers crystallizes out as a salt and this salt is then converted back to the enantiomeric lacid acid, but the enantiomeric product finally obtained will inevitably still contain significant quantities of the other enantiomer.

In European Patent Application 552,255 it is reported that glycolic acid of industrial quality can be crystallized by putting a solution thereof in a freezer, giving rise to crystals which are filtered off. It will be clear that such a method is unsuitable for being carried out on an indutrial scale. Such a method is also applied in DE A 2,810,975.

In WO 00/56693 a method is described for the purification of lactic acid on an industrial scale, the method involving: (a) the distillation under reduced pressure of a concentrated lactic acid solution with a total acid content of at least 95% by weight and a enantiomeric lactic acid content of at least 80% by weight, calculated in terms of the concentrated lactic acid solution, and with a ratio of the lactic acid enantiomers not equal to 1, and (b) subjecting the distilled lactic acid sollution to a crystallization, with formation of pure lactic acid, where the pure lactic acid has a total acid content of at least 99% by weight, a monomeric lactic acid content of at least 98% by weight, a chiral purity of 99% or more, calculated in terms of the total quantity of pure lactic acid, a colour of not more than 10 APHA units and an acceptable odour.

In EP A 733,616 a method for the production of glycolic acid crystals is described in which an aqueous solution of glycolic acid is concentrated, seed crystals are added to the concentrated solution and the solution is cooled.

Disadvantages of the method according to WO 00/56693 are that in particular step (a) of this method requires a great deal of energy and that complicated distillation equipment is required.

The present invention aims to solve this problem and therefore relates to a method for the purification of an α-hydroxy acid on an industrial scale (i.e. a scale of at least 10000 tons per annum), in which an α-hydroxy acid with a colour (fresh) of not more than 10,000 APHA units is subjected to at least two crystallization steps.

Advantages of the present invention are that the method requires little energy and relatively simple equipment can be used.

An α-hydroxy acid means a carbonic acid which is substituted with a hydroxy group on the α carbon atom. The general formula of an α-hydroxy acid is therefore:

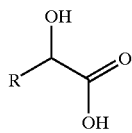

where R is a hydrogen atom, a $C_1$–$C_5$ alkyl group (preferably a methyl group), a $C_6$–$C_{12}$ aryl group or a heterocyclic cycloalky or -aryl group. The α-hydroxy acid according to the invention is preferably lactic acid (R is methyl) or glycolic acid (R is hydrogen) and is in particular lactic acid.

The feed for the method is preferably characterized by a colour (fresh) of not more than 7500 APHA and in particular of not more than 5000 APHA, a total acid content of at least 70% by weight, relative to the whole feed, and a free acid content of at least 60% by weight, relative to the whole feed.

If the α-hydroxy acid is lactic acid, the feed preferably has a total acid content of at least 80% by weight and a free acid content of not more that 10,000 ppm, preferably not more than 5,000 ppm, and a total quantity of residual sugars (predominantly polysaccharides) of not more than 20,000 ppm, preferably not more than 10,000 ppm, where all the contents here indicated are relative to the whole feed. The chiral purity of the feed, if applicable, is at least 90% and preferably at least 95%.

Total acid content (TA) is the acid content after saponification of intermolecular ester bonds with an excess base and is determined by back titration with acid. The total acid content thus gives the quantity of monomeric, dimeric and polymeric lactic acid. The free acid content (FA) is determined by direct titration with base, i.e. before saponification of the intermolecular ester groups. The content of monomeric lactic acid (MM) is here as defined as:

$$MM = TA - 2 \times (TA - FA)$$

provided that TA–FA <10%. This means that not very much dimeric or polymeric lactic acid can b present. It is also assumed that the non-monomeric lactic acid is present in the form of lactoyl lactic acid (dimer).

Chiral purity (for an excess S-isomer) is here defined as:

$$\text{Chiral purity} = 100\% \times \{(\text{S-isomer})/(\text{R-isomer} + \text{S-isomer})\}$$

According to the invention two crystallization steps are preferably carried out, with both crystallization steps preferably being carried out in one device.

The known crystallization techniques can in principle be applied in the method according to the present invention. An example of such a technique is melting crystallization (or cooling crystallization), where the condensed, liquid concentrate or distillate, which for example contains (S)- or (R)-lactic acid in a molten state, is directly cooled, so that the (S)- or (R)-lactic acid crystallizes out. It is preferable to keep the temperature at which crystallization occurs (the crystallation temperature) as low as possible, so that the formation of oligomers and polymers of the α-hydroxy acid is limited as much as possible. According to the invention a concentrate is preferably used, since the preparation of a distillate is unfavourable in terms of process energy.

Melting crystallization is a process in which a crystalline material obtained from a melt of the material to be crystallized. This technique is for example described in detail in Kirk-Othmer, Encyclopedia of Chemical Technology, fourth edition, Part 7, pages 723–727 (1993), in J. W. Mullin, "Crystallization", third revised edition. Butterworth-Heinemann Ltd., pages 309–323 (1993) and in J. Ullrich and B. Kallies, Current Topics in Crystal Growth Research, 1 (1994), which have been recorded here for reference. The main advantages of melting crystallization relative to distillation is that much less energy is needed, because the enthalpy of melting of organic compounds is generally lower than the enthalpy of evaporation. This advantage also occurs with other crystallization techniques, because the enthalpy of crystallization relative to distillation is furthermore that the process can generally be carried out at a much lower temperature—which is advantageous when the organic compound is thermally unstable.

The melting crystallization can be carried out with the aid of a suspension crystallization or a layer crystallization, if necessary in combination with a washing column or a centrifuge, or another purification technique. Examples of suitable equipment and process are described in Kirk-Othmer, Encyclopedia of Chemical Technology, fourth edition, Part 7, pages 723–727 (1993), in J. W. Mullin, "Crystallization", third revised edition, Butterworth-Heinemann Ltd., pages 309–323 (1993) and J. Ullrich and B. Kallies, Current Topics in Crystal Growth Research, 1 (1994), the content of which has been recorded here for reference.

It has also been found that crystallization of an aqueous solution gives very good results. In this crystallization treatment a concentrated lactic acid solution is for example diluted with water and this is then subjected to one or more cooling and/or evaporative crystallization steps. In these techniques the concentrate or distillate is directly cooled (cooling crystallization) or concentrated by evaporation of water (evaporated crystallization). The driving force for the crystallization in the cooling crystallization techniques is the bringing about of supersaturation in the concentrated lactic acid solution by reducing the temperature of the concentrated lactic acid solution. As a resolution of the lower temperature of the solution the solubility decreases and supersaturation occurs.

The driving force for the crystallization in the evaporative crystallization technique is the bringing about of supersaturation in, for example, a concentrated latic acid solution by evaporation of water, so that the concentration of the solution increases while the temperature remains constant. Crystallization of the lactic acid then occurs during the evaporation of water.

Another highly suitable crystallization technique is adiabatic crystallization, where the driving force for the crystallization is the bringing about of supersaturation in, for example, a concentrated lactic acid solution by evaporation of water without supplying heat. The evaporation of water has two effets: (a) the temperature of the concentrated lactic acid solution becomes lower and (b) the concentration of the acid increases. Both effects lead to a decrease in the solubility and an increase in the supersaturation.

The crystallization steps are preferably carried out according to the invention by means of adiabatic crystallization or cooling crystallization, in particular by means of adiabatic crystallization. Seed crystals are preferably added to the feed in the crystallizations. If a solvent is used in the crystallization, this is preferably water.

The α-hydroxy acid which is crystallized out can then be separated by the known methods for solid-liquid separation from the remaining liquid, or mother liquour.

Examples of suitable separation techniques for separating the α-hydroxy acid crystals from the mother liquor are centifugation, decanting, filtration, separation by means of one or more washing columns, or a combination of two or more of these techniques. In the context of the invention it has been found that centrifugation and separation with one or more washing columns is particularly appropriate.

The mother liquors which are obtained still contained considerable quantities of α-hydroxy acid. For optimal process management it is therefore preferable to feed these mother liquors back into the process.

After isolation, the α-hydroxy acid crystals which are obtained are directly dissolved in suitable solvent, usually water, in order to prevent coagulation of the hygroscopic α-hydroxy acid crystals occurring. The concentration of the α-hydroxy acid solution so obtained can in principle have any desired concentration. In practice this will usually vary form 30 to 95%. Concentrations commonly occurring on the market are 80–90%.

The invention also relates to an α-hydroxy acid or an α-hydroxy acid solution with a chiral purity of at least 99% and a colour of not more than 20 APHA units, preferably not more than 10 APHA units, with the α-hydroxy acid or the α-hydroxy acid solution having an acceptable odour, in particular for pharmaceutical applications. In the case of an α-hydroxy acid solution the solvent is preferably water. The chiral purity is preferably at least 99%, in particular at least 99.5%, which corresponds to 99% enantiomeric excess (ee) or higher. Most preferable is chiral α-hydroxy acid, or the solution thereof, whose chiral purity is at least 99.8% (i.e. at least 99.6% ee).

The α-hydroxy acid or the α-hydroxy acid solution also meets the following requirements:
alcohol content: not more than 250 ppm (alcohol is methanol, ethanol or other alcohol, as alcohol as such or in the form of a lactate).
total nitrogen: not more than 15 ppm.
total sugar: not more than 100 ppm.
total polysaccharides: not more than 100 ppm.
organic acids (other than lactic acid): not more than 250 ppm.

With regard to odour the α-hydroxy acid or the α-hydroxy acid solution possesses a considerable improvement for application in foods and a higher chemical purity than the products according to the prior art.

When it is chiral, the α-hydroxy acid according to the invention can be both an S-α-hydroxy acid and a (R)-α-hydroxy acid, depending on the microorganism which is used in the fermentation.

Because of their high chiral purity both the (S)-α-hydroxy acid and the (R)-α-hydroxy acid or the solutions thereof can very suitably be applied for chiral syntheses. The chirally pure (S)-α-hydroxy acid or solutions thereof are also very suitable for being applied in pharmaceutical preparations.

The invention therefore also relates to a pharmaceutical preparation which contains the (S)-α-hydroxy acid or the (S)-α-hydroxy acid solution described above. The invention is now illustrated by means of the following example.

EXAMPLE (S)-lactic acid with the following properties is used as the starting material:

| | |
|---|---|
| Total acid content | 95.4% |
| Free acid content | 91.1% |
| Colour (fresh) | 4850 APHA |
| Total nitrogen | 1080 ppm |
| Total residual sugars | 6490 ppm |
| Chiral purity | 99.61% |

In the first crystallization step a double-walled 2.7 litre vessel was connected with a thermoblast bath and 2045 g of the starting material described above was put into the vessel. The acid was cooled to 40° C. while stirring and inoculated with 0.4 g of a suspension which contained seed crystals. The acid was then cooled from 40° to 30° C. in 5 hours in accordance with a linear colling programme. The crystals formed were rod-shaped and many small particles were formed. After 5 hours the temperature of the thermostat bath was 30° C. and that of the crystal suspension of the acid was 31.9° C. The suspension was centrifuged (Sieva laboratory centrifuge, Hermle). 831 g of crystals and 1061 g of mother liquor was obtained (yield of 46%, calculated in terms of lactic acid).

In a second crystallization step a three-necked round-bottomed flask of 0.5 litre was placed in a thermostat bath and 349 g of the crystals obtained above and 22.3 g of water were put into the flask, so that a suspension was obtained which corresponded to a lactic acid concentration of about 94%. The suspension was heated while stirring in order to dissolve all the crystals and the solution was then cooled to 36° C. while stirring. After that about 0.27 g of a suspension which contained seed crystals was added and the seed crystals were left to grow for 10 minutes at 36° to 24° C. The mixture was then cooled in accordance with a linear programme (from 36° C. to 24° C. in 6 hours). The crystals formed had a cuboid shape. After cooling to 24° C. the suspension was centrifuged: 165 g of crystals were obtained from 356 g of suspension (yield of 49%, calculated in terms of lactic acid). The total yield from the two crystallization steps was 22%, calculated in terms of lactic acid. The crystals from the first and second crystallization were dissolved in water (90% solution) and the solutions were analysed. The results are shown in the table below.

|  | First crystallization | Second crystallization |
|---|---|---|
| Colour (fresh) | 349 APHA | 14 APHA |
| Colour (after heating) | 713 APHA | 18 APHA |
| Total nitrogen | 55 ppm | <10 ppm |
| Total residual sugars | 430 ppm | 40 ppm[a] |
| Chiral purity | 99.97% | >99.99% |

[a]This value is close to the detection limit.

What is claimed is:

1. Method for the purification of a fermentatively prepared α-hydroxy acid on an industrial scale, in which an α-hydroxy acid with a colour (fresh) of not more than 10,000 APHA units is subjected to at least two crystallization steps, with the crystallization steps being carried out with water as a solvent or without any solvent in cooling crystallization devices, melting crystallization devices, evaporative crystallization devices and/or adiabatic crystallization devices.

2. Method according to claim 1, in which the α-hydroxy acid is lactic acid or glycolic acid.

3. Method according to claim 2, in which the α-hydroxy acid is lactic acid.

4. Method according to claim 1, in which two crystallization steps are applied.

5. Method according to claim 4, in which the crystallization steps are carried out in one device.

6. Method according to claim 1, in which the product stream from the crystallization steps is separated into a mother liquor and α-hydroxy acid crystals by means of solid-liquid separation.

7. Method according to claim 1, in which, if applicable, the chiral purity of the α-hydroxy acid is at least 90% with a colour (fresh) of not more than 10,000 APHA units.

8. Method according to claim 1, in which the α-hydroxy acid is prepared fermentatively, with a colour (fresh) of not more than 3000 APHA units.

9. Method according to claim 1, in which the cooling crystallization is carried out by direct cooling of a condensed, liquid concentrate or distillate of the α-hydroxy acid.

10. Method according to claim 1, in which the melting crystallization is carried out by direct cooling of a condensed, liquid concentrate or distillate which contains the α-hydroxy acid in a molten state.

11. Method according to claim 1, in which the evaporative crystallization is carried out by (1) diluting a condensed, liquid concentrate or distillate of the α-hydroxy acid with water and (2) evaporation of water.

12. Method according to claim 1, in which the adiabatic crystallization is carried out by evaporation of water without supplying heat.

* * * * *